US006228362B1

(12) United States Patent
Griffiths et al.

(10) Patent No.: US 6,228,362 B1
(45) Date of Patent: May 8, 2001

(54) BORON NEUTRON CAPTURE THERAPY USING PRE-TARGETING METHODS

(75) Inventors: Gary L. Griffiths, Morristown; Serengulam Govindan, Summit, both of NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

(21) Appl. No.: 09/205,243

(22) Filed: Dec. 4, 1998

Related U.S. Application Data

(63) Continuation-in-part of application No. 08/687,626, filed on Jul. 26, 1996, now Pat. No. 5,846,741, which is a continuation-in-part of application No. 08/486,166, filed on Jun. 7, 1995, now abandoned, and a continuation-in-part of application No. 08/456,393, filed on Jun. 1, 1995, now Pat. No. 5,698,405, which is a division of application No. 07/933,982, filed on Aug. 21, 1992, now Pat. No. 5,525,338.

(60) Provisional application No. 60/090,142, filed on Jun. 22, 1998.

(51) Int. Cl.[7] .................................................. A61K 39/395
(52) U.S. Cl. ................. 424/175.1; 424/1.49; 424/136.1; 424/155.1; 424/175.1; 530/388.8; 530/388.85
(58) Field of Search ............................... 424/1.49, 136.1, 424/155.1, 174.1, 175.1; 530/387.3, 388.8, 388.85, 388.9, 389.8, 389.7

(56) References Cited

U.S. PATENT DOCUMENTS

| 4,624,846 | * | 11/1986 | Goldenberg | 424/1.1 |
|---|---|---|---|---|
| 4,863,713 | | 9/1989 | Goodwin et al. | 424/1.1 |
| 4,925,648 | | 5/1990 | Hansen et al. | 424/1.1 |
| 5,256,395 | | 10/1993 | Barbet et al. | 424/9 |
| 5,274,076 | | 12/1993 | Barbet et al. | 530/300 |

FOREIGN PATENT DOCUMENTS

| 89/10140 | * | 11/1989 | (WO) . |
|---|---|---|---|
| 19273 | | 11/1992 | (WO) . |
| 96 40245 | | 12/1996 | (WO) . |
| 97 29114 | | 8/1997 | (WO) . |
| 98 29114 | | 8/1997 | (WO) . |
| 97 41898 | | 11/1997 | (WO) . |
| 95 04917 | | 2/1998 | (WO) . |

OTHER PUBLICATIONS

Mehta et al., "Targeted Drug Delivery for Boron Neutron Capture Therapy," *Pharmaceutical Research*, 13:344–351 (1996).

Primus et al., "Bispecific Antibody Mediated Targeting of Nido–Carboranes to Human Colon Carcinoma Cells," *Bioconjugate Chemistry*, 7:532–535 (1996).

Pak et al., "Preparation and Properties of Nido–carborane–specific Monoclonal Antibodies for Potential Use in Boron Neutron Capture Therapy for Cancer," *Proc. Natl. Acad. Sci. USA*, 92:6986–90 (1995).

Liu et al, Anticancer Research vol. 16 p. 2581, 1996.*

Primus et al, Bioconjugate Chemistry vol. 7 p. 532, 1996.*

Mehta et al. Abstract—"Interspecies Pharmacokinetic Scaling of Clearance and Volume of Distribution Data for Borocaptate Sodium," *Pharmaceutical Research*, 12(9):S393 (1995).

Mehta et al. "Targeted Drug Delivery For Boron Neutron Capture Therapy," *Pharmaceutical Research*, 13(3):344–51 (Mar. 1996).

Primus et al., "Bispecific Antibody Mediated Targeting of nido–Carboranes to Human Colon Carcinoma Cells," *Bioconjugate Chem.*, 7:532–535 (Jan. 1996).

Songsivilai et al., Biochem. Biophys. Res. Commun. 164: 271 (1989).

Traunecker et al., EMBO J. 10: 3655 (1991).

Weiner et al., J. Immunol. 147: 4035 (1991).

* cited by examiner

*Primary Examiner*—Sheela Huff
(74) *Attorney, Agent, or Firm*—Foley & Lardner

(57) ABSTRACT

The present invention provides a method for targeting boron atoms to tumor cells in a patient. The method includes the steps of (A) administering a targeting composition comprising a conjugate of (i) at least one first antibody or antigen-binding antibody fragment which selectively binds to an antigen produced by or associated with the tumor cells and present at the tumor cells, and (ii) at least one second antibody or antibody fragment which specifically binds to a hapten on a boron compound; (B) optionally, a clearing composition; (C) said boron compound; and (D) optionally, a second clearing composition. The method may further comprise the step of irradiating the boron atoms of the boron compound, thereby effecting BNCT of the tumor cells. Compositions and kits for carrying out the method also are provided.

33 Claims, No Drawings

BORON NEUTRON CAPTURE THERAPY USING PRE-TARGETING METHODS

This application is a continuation-in-part of U.S. application Ser. No. 60/090,142, filed Jun. 22, 1998 and a continuation-in-part of U.S. application Ser. No. 08/687,626, filed Jul. 26, 1996, now U.S. Pat. No. 5,846,741. U.S. application Ser. No.08/687,626 is a continuation-in-part U.S. application Ser. No. 08/486,166, filed Jun. 7, 1995 now abandoned, and of U.S. application Ser. No.08/456,393, filed Jun. 1, 1995, now U.S. Pat. No. 5,698,405, which is a divisional of U.S. application Ser. No. 07/933,982, filed Aug. 21, 1992, now U.S. Pat. No. 5,525,338. The contents of these applications and all other documents cited herein are incorporated by reference herein in their entirety.

BACKGROUND OF THE INVENTION

1. Field of the Invention

The present invention relates to improved methods for targeting boron atoms to tumor cells for effecting boron neutron capture therapy (BNCT). BNCT is a binary system designed to deliver ionizing radiation to tumor cells by neutron irradiation of tumor-localized boron-10 atoms. In the present invention, the cancer cells are pre-targeted, for example, with a multivalent antibody conjugate wherein at least one antibody or antibody fragment specifically targets tumor cells and at least one antibody or antibody fragment specifically binds to a boron compound. Then, the boron compound is administered and is bound by the multivalent antibody conjugate localized at the cancer site. The localized boron may then be irradiated, thereby effecting treatment of the tumor cells.

2. Description of Related Art

BORON NEUTRON CAPTURE THERAPY

Boron neutron capture therapy (BNCT) is based on the nuclear reaction which occurs when a stable isotope, B-10 (present in 19.8% natural abundance), is irradiated with thermal neutrons to produce an alpha particle and a Li-7 nucleus. These particles have a path length of about one cell diameter, resulting in high linear energy transfer. Just a few of the short-range 1.7 MeV alpha particles produced in this nuclear reaction are sufficient to target the cell nucleus and destroy it. Barth et al., *Cancer*, 70: 2995–3007 (1992). Since the $^{10}B(n,\alpha)^7Li$ reaction will occur, and thereby produce significant biological effect, only when there is a sufficient fluence (number) of thermal neutrons and a critical amount of B-10 localized around or within the malignant cell, the radiation produced is localized. The neutron capture cross section of B-10 far exceeds that of nitrogen and hydrogen found in tissues, which also can undergo capture reactions, (relative numbers: 1 for N-14, 5.3 for H-1, and 11560 for B-10), so that once a high concentration differential of B-10 is achieved between normal and malignant cells, only the latter will be affected upon neutron irradiation. This is the scientific basis for boron neutron capture therapy. Barth et al., supra; Barth et al. *Cancer Res.*, 50: 1061–70 (1990); Perks et al., *Brit. J. Radiol.*, 61: 1115–26 (1988).

Nuclear reactors are the source of neutrons for BNCT. Thermal neutron beams with energies in the range of 0.023 eV, used in early experiments for treating brain tumors, are easily attenuated by tissues, and are poorly penetrating. More recent advances with neutrons of intermediate energy (epithermal neutrons, 1–10,000 eV energy) have led to the consensus for its use in planned clinical trials in the US and Europe. Alam et al., *J. Med. Chem.*, 32: 2326–30 (1989). Fast neutrons with a probable energy of 0.75 MeV are of little use in BNCT.

Original calculations estimated that a boron concentration of 35–50 µg per gram of tumor, or $10^9$ B-10 atoms per tumor cell, would be necessary to sustain a cell-killing nuclear reaction with thermal neutron fluences of $10^{12}$–$10^{13}$ n.cm$^{-2}$. Fairchild et al., *Int. J. Radiat. Oncol. Biol. Phys.*, 11: 831 (1985). These calculations were based on uniformly distributed boron, as seen with non-specific boronated compounds. For antibody-based boron agents, assuming saturation of all surface antigens on the tumor cell, this level of boron requirement translates to about 1000 atoms per antibody molecule. However, more recent Monte Carlo calculations led to the analysis that for a non-internalizing antibody, boron loading could be as low as 300 atoms per MAb molecule. Kalend et al, *Med. Phys.*, 18: 662 (1991); Zamenhof et al., *J. Nat'l Cancer Inst.*, 84: 1290–91 (1992).

This was based on the following rationale: for tumor cells exhibiting a nucleus-to-cell volume ratio of 0.5 and an effective cell diameter of 10 µm, three B-10 fissions on the cell surface would produce at least one heavy particle trajectory into the nucleus. Assuming saturation of antigen sites on the cell surface, it was deduced that under these conditions just 300 atoms per antibody molecule would suffice to bring about the three fission reactions on the tumor cell surface. The present invention describes a method which can attach a 20-fold greater number of boron atoms per MAb than these prior methods entailed.

Historically, BNCT was first employed for the treatment of glioblastoma (a fatal form of brain tumor) and other brain tumors at a time when tumor specific substances were almost unknown. Hatanaka et al., in *BORON NEUTRON CAPTURE THERAPY FOR TUMORS*, pp.349–78 (Nishimura Co., 1986). One of the first boronated compounds employed, a sulfhydryl-containing boron substance called sodium borocaptate or BSH ($Na_2, B_{12}H_{11}SH$), crosses the blood-brain barrier to localize in brain, and this has been the anatomical basis for neutron capture therapy of brain tumors. Clinical trials have been carried out, or are scheduled, for the treatment of gliomas in Japan, the US and Europe. Barth et al., *Cancer*, supra. Problems with previous inorganic boron therapy methods was that the boron reached both targeted and non-target areas. Accordingly, when the boron was irradiated, healthy cells as well as cancerous cells were destroyed.

The BNCT concept has been extended to other cancers, spurred on by the discovery of a number of tumor-localizing substances, including tumor-targeting monoclonal antibodies. For instance, boronated amino acids such as p-boronophenylalanine accumulated in melanoma cells. The potential of using boronated monoclonal antibodies directed against cell surface antigens, such as CEA, for BNCT of cancers has been demonstrated. Ichihashi et al., *J. Invest. Dermatol*, 78: 215–18 (1982); Goldenberg et al., *P.N.A.S., USA*, 81:560–63 (1984); Mizusawa et al. *P.N.A.S., USA*, 79: 3011–14 (1982); Barth et al., *Hybridoma*, 5(supp. 1): 543–5540 (1986); Ranadive et al. *Nuci. Med. Biol.*, 20: 663–68 (1993). However, heavily boronated antibodies failed to target tumor in vivo in animal models. Alam et al., supra; Barth et al., *Bioconjugate Chem.*, 5: 58–66 (1994).

Success with BNCT of cancer requires methods for localizing a high concentration of boron-10 at tumor sites, while leaving non-target organs essentially boron-free. Non-antibody boronated compounds which accumulate in tumor preferentially, but not specifically, have the disadvantage that tumor-to-blood and tumor-to-organ ratios are often less than ideal, with the result that damage to normal organs could occur during irradiation with neutron beams.

In the case of antibodies, the perceived need to load the same with 1000 boron atoms per antibody molecule has led to the design of a variety of heavily boronated antibodies using, for instance, polylysine, dendrimer or dextran as intermediate carriers of boron clusters. Alam et al., supra; Barth et al., *Bioconjugate Chem.*, supra. Although in many instances some antigen-binding was found to be retained in vitro, these boronated conjugates predominantly localized in liver with little accretion in tumor in in vivo animal tumor models.

Thus, there is need for a method of targeting boron atoms to tumor cells that is able to deliver a large amount of boron atoms to tumor sites, while leaving noncancerous sites relatively boron-free.

PRE-TARGETING

The concept of pre-targeting for in vivo imaging application was proposed by Hnatowich et al., *J. Nucl. Med.*, 28: 1294–1302 (1987), and was later examined from a theoretical viewpoint. Van Osdol et al., *J. Nucl. Med.*, 34: 1552–64 (1993). Pre-targeting has been recently reported to have resulted in very encouraging preclinical results with yttrium-90 radioimmmunotherapy. Axworthy et al., *J. Immunother.*, 16: 158 (1994). U.S. application Ser. No. 07/933,982 (filed Aug. 21, 1992, issue fee paid Dec. 28, 1995), U.S. Pat. No. 5,482,698, U.S. application Ser. No. 08/409,960 (filed Mar. 25, 1995, pending), and U.S. application Ser. No. 08/486, 166 (filed Jun. 7, 1995, pending) also disclose various pre-targeting methods. The contents of all of these references are incorporated herein in their entirety by reference.

Therapy requires a high absolute accretion of the therapeutic agent at the cancer site, as well as a reasonably long duration of uptake and binding. High background levels of non-targeting antibody have long been recognized as a major impediment to high target: background ratios being achieved. To overcome this impediment, various methods have been developed, such as those described in Hansen et al., U.S. Pat. No. 3,927,193 and Goldenberg, U.S. Pat. Nos. 4,331,647, 4,348,376, 4,361,544, 4,468,457, 4,444,744, 4,460,459, 4,460,561, 4,624,846 and 4,818,709, the disclosures of all of which are incorporated herein by reference.

Pre-targeting methods using biotin/avidin approaches are described, for example, in Hnatowich et al., *J. Nucl. Med.* 28: 1294, 1987; Oehr et al., *J. Nucl. Med.* 29: 728, 1988; Klibanov et al., *J. Nucl. Med.* 29: 1951, 1988; Sinitsyn et al., *J. Nucl. Med.* 30: 66, 1989; Kalofonos et al, *J. Nuc. Med.* 31: 1791, 1990; Schechter et al., *Int. J. Cancer* 48: 167, 1991; Paganelli et al., *Cancer Res.* 51: 5960, 1991; Paganelli et al., *Nucl. Med. Commun.* 12: 211, 1991; Stickney et al., *Cancer Res.* 51: 6650, 1991; and Yuan et al., *Cancer Res.* 51: 3119, 1991; all incorporated herein in their entirety by reference.

Pre-targeting a target site with a targeting protein, such as an antibody or an antibody fragment, conjugated to an antibody or antibody fragment specific for the second conjugate also has been described. U.S. Pat. Nos. 5,274,076, 4,863,713 and 5,256,395.

These methods involve pre-targeting a target site, such as a tumor or lesion, with a targeting protein, such as an antibody or antibody fragment, conjugated to one member of a binding pair, such as biotin, avidin, or a second antibody, whereby the antibody conjugate localizes at the target site. Then, a conjugate of a detection or therapeutic agent, such as a radioisotope, and the complementary member of the binding pair, such as avidin, biotin, or a corresponding hapten is administered. The binding affinity between the members of the binding pair causes the second conjugate to localize at the target site, where the first conjugate already is bound.

In some of these methods, an intermediate clearing or localizing step is used. In this case, the first conjugate comprises one member of the binding pair (for example, biotin), the clearing and localizing agent may comprise the other member of the binding pair (for example, avidin), and the second conjugate comprises the same member of the binding pair as the first (for example, biotin). Other clearing agents, such as antibodies, also have been described.

There is a need for a method of targeting boron atoms to tumor cells that obtains high tumor:non-tumor ratios of the boron atoms, and that delivers sufficient amounts of boron atoms to tumor sites in an efficient manner. Compositions suitable for use in such a method also are needed.

SUMMARY OF THE INVENTION

It is therefore an object of the present invention to provide a method for targeting boron atoms to tumor cells that overcomes the previous problems of maintaining a high tumor:non-tumor ratio of boron-10 atoms, and for delivering sufficient amounts of boron-10 atoms to tumor sites efficiently, and to provide compositions for use in this method.

In accomplishing these and other objects of the invention, there is provided, in accordance with one aspect of the present invention, a method for targeting boron atoms to tumor cells in a patient, comprising the steps of: (A) administering to the patient a targeting composition comprising a conjugate of (i) at least one first antibody or antigen-binding antibody fragment which selectively binds to an antigen produced by or associated with the tumor cells and present at the tumor cells, and (ii) at least one second antibody or antibody fragment which specifically binds to a hapten on a boron compound, and allowing the conjugate to localize at the tumor cells; (B) optionally, administering to the patient a first clearing composition, and allowing the clearing composition to clear non-localized conjugate from circulation; (C) administering to the patient the boron compound and allowing the boron compound to localize at the tumor cells; (D) optionally, administering to the patient a second clearing composition, and allowing the clearing composition to clear non-ocalized boron compound from circulation.

The method may further comprise the step of irradiating the boron atoms of the boron compound localized at the tumor cells, thereby effecting BNCT of the tumor cells.

In one embodiment of the present invention, the boron compound is radiolabeled with a detectable label, in which case the method may further comprise the step of detecting the detectable label of the boron compound. In accordance with one aspect of this embodiment, the boron atoms of the boron compound localized at the tumor cells are irradiated after the detectable label is detected.

In accordance with another aspect of the present invention there is provided a sterile, injectable composition for human use comprising a composition for use in targeting boron atoms to tumor cells, comprising a conjugate of (i) at least one first antibody or antigen-binding antibody fragment which selectively binds to an antigen produced by or associated with the tumor cells and present at the tumor cells, and (ii) at least one second antibody or antibody fragment which specifically binds to a hapten on a boron compound.

In accordance with another aspect of the present invention, there is provided a kit suitable for use in a method for targeting boron atoms to tumor cells in a patient, the kit comprising: (A) a sterile, injectable preparation of a targeting composition comprising a conjugate of (i) at least one first antibody or antigen-binding antibody fragment which selectively binds to an antigen produced by or associated with the tumor cells and present at the tumor cells, and (ii) at least one second antibody or antibody fragment which specifically binds to a hapten on a boron compound; (B) optionally, a first clearing composition; (C) a boron compound; and (D) optionally, a second clearing composition.

Additional objects and advantages of the invention are set forth in part in the description that follows, and in part will be obvious from the description, or may be learned by practice of the invention. The objects and advantages may be realized and obtained by means of the processes and compositions particularly pointed out in the appended claims.

DETAILED DESCRIPTION

The present invention overcomes the aforementioned problems with antibody-targeted BNCT by decoupling the antibody and boron delivery steps by using, for example, a two- or three-step pre-targeting procedure. While prior methods of antibody-targeted BNCT involve loading about 1500 boron-10 atoms onto a single molecule of antibody, the present invention does not load the targeting antibody with boron, thereby eliminating the problems associated with boron-mAb hyper-substitution.

In accordance with one aspect of the present invention, a high concentration of boron is specifically localized at the tumor cells by pre-targeting the tumor cells with a monoclonal, multispecific antibody conjugate. At least one first antibody or antibody fragment of the conjugate selectively binds to an antigen produced by or associated with tumor cells, and at least one second antibody or antibody fragment of the conjugate specifically binds to a hapten on the boron compound. The use of monoclonal, multispecific antibodies to pre-target tumor cells greatly enhances the efficacy of BNCT over previously used boronated compounds which accumulated in tumor cells preferentially, but not selectively. Moreover, the strong affinity between the second antibody or antibody fragment and the boron compound increases the efficiency of the delivery of boron to the tumor cells.

The specificity of BNCT also may be enhanced by administering a clearing agent following the localization of the targeting conjugate at the tumor cells. The use of a clearing agent ensures the rapid removal of unbound targeting conjugate. This enhancement may be further improved by the administration of an anti-idiotypic clearing agent, such as an anti-idiotypic monoclonal antibody specific for the determinant of the targeting conjugate which binds to the tumor site. One advantage of using such a clearing agent is that it does not competitively remove bound targeting conjugate from the target site, as may occur with other clearing agents. As a result, a higher level of boron is ultimately delivered to the tumor cells. The clearance effect may be further enhanced by using a galactosylated clearing agent, because a galactosylated clearing agent is rapidly cleared through the liver.

The specificity of the therapy may be further enhanced by radiolabelling the boron compound with a detectable label. This enhancement allows the practitioner to determine the location of the boron before it is irradiated and permits the practitioner to delay irradiation until all non-localized boron has been removed from the body, thereby minimizing undesirable tissue damage. Radiolabelling the boron compound with a detectable label also facilitates focusing the thermal neutron beam used to irradiate the boron molecules, further maximizing the benefits of boron therapy and further reducing unintended tissue damage.

The specificity of BNCT may be further enhanced by performing a clearing step after the boron compound has been administered. This step may be performed in addition to or instead of the clearance step discussed above, and comprises administering a clearing agent with specificity for the boron compound. Any suitable clearing agent may be used. Advantageously, the clearing agent comprises an antibody, such as an antibody specific for the hapten on the boron compound recognized by the second antibody or antibody fragment of the targeting conjugate. This clearance may be further enhanced by galactosylating the clearing agent, as discussed above. This clearing step facilitates the rapid removal of non-localized boron compounds, which further reduces the likelihood of unintended tissue damage.

A method comprising one or more of the above described features will achieve BNCT with greater specificity and efficacy than has heretofore been possible.

As mentioned above, the present invention uses multivalent antibody conjugates to target boron to tumor cells. The targeting composition comprises a conjugate of at least one first antibody or antigen-binding antibody fragment which selectively binds to an antigen produced by or associated with the tumor cells and present at the tumor cells, and at least one second antibody or antibody fragment which specifically binds to a hapten on the boron compound.

Bispecific antibodies can be made by a variety of conventional methods, e.g., disulfide cleavage and reformation of mixtures of whole IgG or, preferably $F(ab')_2$ fragments, fusions of more than one hybridoma to form polyomas that produce antibodies having more than one specificity, and by genetic engineering. Bispecific antibodies have been prepared by oxidative cleavage of Fab' fragments resulting from reductive cleavage of different antibodies. This is advantageously carried out by mixing two different $F(ab')_2$ fragments produced by pepsin digestion of two different antibodies, reductive cleavage to form a mixture of Fab' fragments, followed by oxidative reformation of the disulfide linkages to produce a mixture of $F(ab')_2$ fragments including bispecific antibodies containing a Fab' portion specific to each of the original epitopes (i.e., tumor-associated antigen and antigen or hapten present on the boron compound). General techniques for the preparation of multivalent antibodies may be found, for example, in Nisonoff et al., Arch Biochem. Biophys. 93: 470 (1961), Hammerling et al., J. Exp. Med. 128: 1461 (1968), and U.S. Pat. No. 4,331,647.

A more selective linkage can be achieved by using a heterobifunctional linker such as maleimide-hydroxysuccinimide ester. Reaction of the ester with an antibody or antibody fragment will derivatize amine groups on the antibody or antibody fragment, and the derivative can then be reacted with, e.g., an antibody Fab fragment having free sulfhydryl groups (or, a larger fragment or intact antibody with sulfhydryl groups appended thereto by, e.g., Traut's Reagent). Such a linker is less likely to crosslink groups in the same antibody and improves the selectivity of the linkage.

It is advantageous to link the antibodies or fragments at sites remote from the antigen binding sites. This can be accomplished by, e.g., linkage to cleaved interchain sulfhydryl groups, as noted above. Another method involves reacting an antibody having an oxidized carbohydrate portion with another antibody which has at lease one free amine function. This results in an initial Schiff base (imine) linkage, which is preferably stabilized by reduction to a secondary amine, e.g., by borohydride reduction, to form the final product. Such site-specific linkages are disclosed, for small molecules, in U.S. Pat. No. 4,671,958, and for larger addends in U.S. Pat. No. 4,699,784.

Alternatively, bispecific antibodies can be produced by fusing two hybridoma cell lines that produce anti-tumor-associated antigen Mab and anti-boron compound Mab. Techniques for producing tetradomas are described, for example, by Milstein et al., Nature 305: 537 (1983) and Pohl et al., Int. J. Cancer 54: 418 (1993).

Bispecific antibodies also can be produced by genetic engineering. For example, plasmids containing DNA coding for variable domains of an anti-tumor-associated antigen Mab can be introduced into hybridomas that secrete antibodies to the boron compound. The resulting "transfectomas" produce bispecific antibodies that bind tumor-associated antigen and the boron compound. Alternatively, chimeric genes can be designed that encode both anti-tumor-associated antigen and anti-boron compound binding domains. General techniques for producing bispecific antibodies by genetic engineering are described, for example, by Songsivilai et al., Biochem. Biophys. Res. Commun. 164: 271 (1989); Traunecker et al., EMBO J. 10: 3655 (1991); and Weiner et al., J. Inumunol. 147: 4035 (1991).

A higher order multivalent, multispecific molecule can be obtained by adding various antibody components to a bispecific antibody, produced as above. For example, a bispecific antibody can be reacted with 2-iminothiolane to introduce one or more sulfhydryl groups for use in coupling the bispecific antibody to a further antibody derivative that binds at the same or a different epitope of the tumor-associated antigen or of the boron compound, using the bis-maleimide activation procedure described above. These techniques for producing multivalent antibodies are well known to those of skill in the art. See, for example, U.S. Pat. No. 4,925,648, and Goldenberg, international publication No. WO 92/19273, which are incorporated by reference.

The targeting composition may comprise a conjugate comprising a plurality of antibodies or antibody fragments that specifically bind to the same or different epitopes of a tumor-associated antigen, or that bind to different tumor-associated antigens. Additionally or alternatively, the conjugate may comprise a plurality of antibodies or antibody fragments that specifically bind to the same or different epitopes of the boron compound.

In accordance with one aspect of this embodiment of the invention, monoclonal antibodies or fragments of monoclonal antibodies are used. Monoclonal antibodies are preferred because of their high specificities. They are readily prepared by what are now considered conventional procedures of immunization of mammals with immunogenic antigen preparation, fusion of immune lymph or spleen cells with an immortal myeloma cell line, and isolation of specific hybridoma clones. More unconventional methods of preparing monoclonal antibodies are not excluded, such as interspecies fusions and genetic engineering manipulations of hypervariable regions, since it is primarily the antigen specificity of the antibodies that affects their utility in the present invention.

Additionally or alternatively, humanized antibodies or fragments of humanized antibodies are used. Humanized monoclonal antibodies are produced by transferring mouse complementary determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, in Orlandi et al., Proc. Nat'l Acad. Sci. USA 86:3833 (1989). Techniques for producing humanized Mabs are described, for example, in Jones et al., Nature 321:522 (1986); Carter et al, Proc. Nat'l Acad. Sci. USA 89:4285 (1992); Sandhu, Crit. Rev. Biotech. 12:437 (1992), and Singer et al., J. Immun. 150:2844 (1993). See also Shevitz et al., J. Nucl. Med. 35:112 (1994), describing hMN-14, a humanized an anti-CEA antibody having the human IgG$_1$/k isotype. See also co-pending U.S. applications Ser. Nos. 09/091,466, 09/155,106, and 09/155,107, the entire contents of which are incorporated herein by reference. It will be appreciated that newer techniques for production of monoclonals can also be used, e.g., interspecies monoclonals, chimeric (e.g., human/mouse) monoclonals, genetically engineered antibodies and the like.

Antibody fragments useful in the present invention include F(ab')$_2$, F(ab)$_2$, Fab', Fab, Fv and the like, including hybrid fragments. Preferred fragments are Fab', F(ab')$_2$, Fab, and F(ab)$_2$. Also useful are any sub fragments retaining the hypervariable, antigen-binding region of an immunoglobulin and having a size similar to or smaller than a Fab' fragment. This includes genetically engineered and/or recombinant proteins, whether single-chain or multiple-chain, which incorporate an antigen-binding site and otherwise function in vivo as targeting vehicles in substantially the same way as natural immunoglobulin fragments. Such single-chain binding molecules are disclosed in U.S. Pat. No. 4,946,778, which is hereby incorporated by reference. Fab' antibody fragments may be conveniently made by reductive cleavage of F(ab')$_2$ fragments, which themselves may be made by pepsin digestion of intact immunoglobulin. Fab antibody fragments may be made by papain digestion of intact immunoglobulin, under reducing conditions, or by cleavage of F(ab)$_2$ fragments which result from careful papain digestion of whole immunoglobulin. The fragments may also be produced by genetic engineering.

It should be noted that mixtures of antibodies, antibody fragments and immunoglobulin classes can be used, as can hybrid antibodies. Multispecific, including bispecific and hybrid, antibodies and antibody fragments are useful in the methods of the present invention, and are comprised of at least two different substantially monospecific antibodies or antibody fragments, wherein at least two of said antibodies or antibody fragments specifically bind to at least two different antigens produced by or associated with the cancer cells or at least two different epitopes or molecules of a marker substance produced by or associated with the cancer cells. Multispecific antibodies and antibody fragments with dual specificities can be prepared analogously to the anti-tumor marker hybrids disclosed in U.S. Pat. No. 4,361,544. Other techniques for preparing hybrid antibodies are disclosed in, e.g., U.S. Pat. No. 4,474,893 and 4,479,895, and in Milstein et al., Immunol. Today, 5: 299 (1984).

Preferred are antibodies having a specific immunoreactivity to a marker substance produced by or associated with the cancer cells of at least 60% and a cross-reactivity to other antigens or non-targeted substances of less than 35%.

Antibodies against tumor antigens are known. For example, antibodies and antibody fragments which specifically bind markers produced by or associated with tumors have been disclosed, inter alia, in Hansen et al., U.S. Pat. No. 3,927,193, and Goldenberg, U.S. Pat. Nos. 4,331,647, 4,348,376, 4,361,544, 4,468,457, 4,444,744, 4,818,709 and 4,624,846. In particular, antibodies against an antigen, e.g., a gastrointestinal, lung, breast, prostate, ovarian, testicular, brain or lymphatic tumor, a sarcoma or a melanoma, are advantageously used.

An antibody preferred for use in the present invention is MN-14, a second generation CEA-antibody that has ten times more affinity for CEA than the first generation version, NP-4. Hansen et al., Cancer, 71: 3478–85 (1993). MN-14 internalizes slowly, making it suitable for a pre-targeting approach.

The antibody or antibody fragment that specifically binds to a hapten on the boron compound may bind to any hapten on the boron compound, including a hapten on a moiety appended to the boron-carrier compound or a hapten of the carrier itself. Examples of suitable antibodies include:

an anti-carborane antibody.

an anti-biotin antibody.

an anti-DTPA Mab, such as the MAb designated 734. See LeDoussal et al., Cancer Res., 50: 3445–52 (1990).

an anti-DTPA Mab, such as the MAb designated DTIn1. See Kranenborg et al., Cancer Res., 55: 5864–67 (1995).

an antibody to a non-chelate hapten such as histamine-succinate. See Janevik-Ivanovska et al., Bioconjugate Chem., 8: 526–33 (1997).

antibodies to the dinitrophenyl (DNP) group such as those disclosed in Eshhar et al., J. Immunol., 124: 775 (1980).

antibodies to polymers such as polyhistidine. See Sigma Catalog (1997).

antibodies to fluorescein isothiocyanate. See W. Hijmans et al., Clin. Exp. Immunol., 4: 457 (1969). If the boron compound comprises other fluorochromes such as rhodamine, Hoecsht 33258 (Aldrich Chem. Co.), or Texas Red, antibodies to haptens on these compounds also could be used.

antibodies to dextran. See Anastase et al., J. Chromatogr. B. Biomed. Appl. 1996 Nov 15; 686(2):141–50. Antigen-binding fragments of the above antibodies also may be used in the present invention.

Cancer states that can be targeted and treated in accordance with the present invention include carcinomas, melanomas, sarcomas, neuroblastomas, leukemias, lymphomas, gliomas and myelomas.

The antibodies and antibody fragments useful in the methods of the present invention may conjugated by a variety of methods known in the art. Many of these methods are disclosed in the above-referenced U.S. Patents and Patent Applications. See also Childs et al, J. Nuc. Med., 26: 293 (1985).

The present invention also provides a boron compound comprising a carrier coupled to approximately 1,500 boron atoms. The carrier may be, for example, dextran. Other carrier molecules will be apparent to those skilled in the art and include aminodextrans, Shih et al., U.S. Pat. No. 5,057,313, other polysaccharides, natural and synthetic polypeptides, such as polylysines, polyglutamic acids and polycysteines, and synthetic polymers, such as polyethyleneimine, polyolefins, polyalcohols, polycarboxylic acids and starburst dendrimers. Another example of suitable carriers are copolymers, such as those with the formula $(Lys)_n$-$(aax)_q$-$(Glu)_m$-$(aay)_p$, where n, m, p and q are integers and aax and aay are non-specified amino acids which may be the same as or different from each other, and which are selected from the natural amino acids and their D-isomers.

In a preferred embodiment of the present invention, sulfhydryl-containing boron moieties, sodium borocaptate or BSH ($Na_2B_{12}H_{11}SH$), are used for boronating dextran. These have been documented to be non-toxic. Barth, Cancer Res., supra; Haselberger et al., Cancer Res. 54: 6318–20 (1994). These are preferably boron-10 enriched, containing, for example up to 95–98 % boron-10.

Preparation of a borocaptate-dextran conjugate is illustrated in Scheme I below. Other boron-10 enriched compounds also are known, such as boron-10-enriched carboranes. Examples of these are described in U.S. Pat. No. 4,824,659, the contents of which are incorporated herein by reference in their entirety. These compounds may be used in accordance with the present invention, for example, by conjugating the carboranes to the chosen carrier. In this embodiment, the second antibody or antibody fragment may specifically bind to the carborane moiety on the boron compound.

In one embodiment, the boron compound comprises biotin. For example, from about 1 to about 3 biotin moieties may be conjugated to a dextran carrier. The biotin is preferably a biotinidase-resistant biotin analog, described in more detail below. In this embodiment, the second antibody or antibody fragment may specifically bind to the biotin moiety on the boron compound. While endogenous biotin is found at high levels in animals, it is believed to occur at lower levels in humans. Accordingly, binding between the targeting conjugate and endogenous biotin is not expected to present a problem in the treatment of humans. Moreover, those slilled in the art can address any problems posed by endogenous biotin by, for example, administering the boron compound shortly after the targeting conjugate is administered. For example, it is believed that administering the boron compound within two to three days of the targeting conjugate would minimize any problems associated with endogenous biotin.

The boron compound of the present invention amplifies the amount of boron that can be delivered per antibody molecule used in the first pre-targeting step, and is an important advantage of the present invention. The use of this compound in accordance with the present invention achieves or surpasses the high boron concentration in tumor required for effective BNCT. Accordingly, the compositions and methods of the present invention are useful for targeting boron atoms to tumor sites for therapy of common malignant tumors by BNCT.

In a preferred embodiment, the boron compound also is radiolabeled with a detectable label. This permits the determination of the location of the administered boron compound. Suitable radiolabels are known to those skilled in the art, and include, for example, gamma-emitting isotopes. The compound may be labelled by methods known in the art. For example, the boron compound may be conjugated to a chelating agent such as, for example, DTPA, which chelates the radiolabel, or a thiol ligand for direct labeling by Tc-99m using known methods, such as those described in U.S. Pat. No. 5,514,363. If DTPA is used to chelate the label, the chelate can serve as a hapten for a bispecific antibody, as disclosed in, e.g., U.S. Pat. No. 5,256,395. When a radiolabeled boron compound is used, the radiolabel can be detected before the boron is irradiated to ensure that the compound has localized at the tumor cells and that non-localized boron has cleared from circulation. This embodiment minimizes the risks of damaging healthy cells when the boron is irradiated, because irradiation can be delayed until the boron compound has localized at tumor cells. The neutron beam advantageously is focused to sites of localized boron-10 moieties to further improve the precision of neutron capture.

Routes of administration of the compositions used in the present invention include intravenous, intra arterial, intrapleural, intraperitoneal, intrathecal, subcutaneous or by perfusion.

In one embodiment of the present invention, a two-step pre-targeting approach is used. As with the other embodiments of the invention, this approach separates the antibody localization step from the step of depositing boron at the tumor sites. For example tumor sites are pre-targeted with a composition comprising a conjugate of a first member a binding pair and an antibody, wherein the antibody binds to antigens produced by or associated with the tumor cells. After a time period for tumor targeting has passed a boron compound comprising a conjugate comprising a complementary member of the binding pair and boron atoms, is administered. This compound binds to the targeting composition localized at the tumor sites, thereby delivering boron atoms to the tumor sites. This method avoids concerns about the in vivo behavior of boronated antibodies because the boron compound does not comprise an antibody. After the boron compound has localized at the tumor site, the boron atoms may be irradiated according to conventional BNCT methods, thereby effecting therapy of the tumor cells.

Another embodiment of the present invention uses an intermediate step between the antibody conjugate delivery step and the boron delivery step. In this step, a clearing agent is used to effect the rapid clearance of circulating antibody and minimize the final boron concentration in circulation. In one embodiment, the clearing agent is an antibody that is anti-idiotypic to the first antibody or antibody fragment of the targeting composition, as described in U.S. application Ser. No. 08/486,166. This antibody may be galactosylated to achieve rapid clearance by asialoglycoprotein receptors in the liver.

In one embodiment of the invention, an anti-idiotypic clearing agent is used, the boron compound is administered, and the patient is exposed to a thermal neutron beam shortly after the boron compound is administered, for example, immediately after the boron compound is administered, thereby irradiating the boron atoms at a time when the amount of boron localized at the targeted tumor cells is at a maximum. In a variation of this embodiment, the boron compound is labeled with a detectable label, and the detectable label is detected prior to the irradiation of the boron atoms. This latter variation allows the practitioner to ensure that the boron compound is localized before the boron is irradiated, thereby minimizing the risks of damage to healthy cells.

Alternatively, the boron compound can be administered parenterally within 24 hrs of the second (clearing) step, or up to 3 days later. The longer the delay after the first step, the lower the amount (and ratio) of clearing agent needed.

The multispecific antibody conjugate may be injected parenterally, usually at a dose of up to 1 g of the first antibody or antibody fragment, for example within a dose range of from about 50 mg to about 500 mg. This can be administered as a single injection or in divided doses.

After 1–5 days, more preferably at less than 2 days and even at less than 1 day when the targeting composition comprises a small and rapidly targeting molecule, such as an antibody fragment or subfragment, a dose of unlabeled clearing agent may be administered parenterally. The dose may be, for example, 2.5 to 10 times the dose of the first step (which can be determined also by measuring the amount of antibody from the first step circulating in the blood at the time of the second step's injection). The clearing agent can be given as a single injection or in divided doses, wherein administering the clearing agent in 2 doses is preferred in certain circumstances. Then, the boron compound is administered with the appropriate time and dosage determined as described above.

Another embodiment of the present invention uses an intermediate step between the boron delivery step and the neutron irradiation step. In this step, a clearing agent is used to effect the rapid clearance of circulating boron compound and to minimize the amount of boron compound in circulation at the time of radiation. Any clearing agent may be used. Advantageously, the clearing agent comprises an antibody specific for the same hapten of the boron compound that is bound by the second antibody or antibody fragment of the targeting composition. An advantage of using such a clearing agent is that it does not competitively remove bound boron compound from the target site. The clearing agent may be galactosylated to achieve rapid clearance as described above.

As discussed above, galactosylated clearing agents remove unlocalized conjugates from circulation and direct them to the liver. When the target site is at or near the liver, further precautions may be taken to avoid unintended tissue damage to the liver during irradiation. For example, the second clearing step can be omitted, a low molecular weight clearing agent can be used to promote clearance through the kidneys, or the practitioner can wait an appropriate amount of time before irradiating the boron to allow the cleared boron compound to pass through the liver.

The timings of the two or three pre-targeting steps can be optimized to enhance the efficiency of boron delivery. The time of maximum tumor uptake of the targeting compositions can be determined by first determining the optimum dose, and also determining the time of maximum tumor uptake at this dose. This may be, for example, between 48 and 72 hours. Optimally, the clearing agent, such as an anti-idiotypic antibody, is administered at this time.

From initial studies, the present inventors have shown that the blood level of the targeting antibody conjugate drops dramatically at the 'zero' time upon administering an anti-idiotypic clearing agent. That is, circulating conjugate is cleared virtually instantaneously. The boron compound, therefore, may be administered within hours (2–4 hours) of the clearance step, and may be administered immediately after the clearance step when an anti-idiotypic clearing agent is used.

The attainment of low levels of circulating boron, and, in particular, the attainment of near absolute clearance of circulating boron, has the advantage of reducing the systemic toxicity observed when boron atoms are irradiated by the neutron beam. That is, because little or no boron is in circulation, only targeted tumor cells are affected by the irradiation of boron atoms by the neutron beam.

In one embodiment of the invention, no clearing agent is used, and the boron compound is administered from about 5 to about 20 days after the administration of the targeting antibody conjugate. This embodiment is advantageous for patients who show rapid blood clearance and tumor accretion of the targeted compounds, for example, because they have a heavy tumor burden which is expressing large amounts of antigen.

The embodiments of the invention are further illustrated through examples which show aspects of the invention in detail. These examples illustrate specific elements of the invention and are not to be construed as limiting the scope thereof.

EXAMPLES

I. PREPARATION OF REAGENTS

Preparation of Bispecific Antibody:

The interchain disulfide bridges of an F(ab')$_2$ fragment having specificity for a tumor-associated antigen (i.e., an antigen produced by or associated with the tumor cells and present at the tumor cells) is gently reduced with cysteine, taking care to avoid light-heavy chain linkage, to form Fab'-SH fragments. The SH group(s) are activated with an excess of bis-maleimide linker (1,6-bis-maleimidohexane). An antibody specific for the boron compound is converted to Fab'-SH and then reacted with the activated target-specific Fab'-SH fragment to obtain a bispecific antibody.

Preparation of a biotin-dextran-boron compound:

1. Preparation of a sulfhydrylborane-dextran conjugate (compound 3 in Scheme I):

70,000 MW dextran is boronated with borocaptate using a published 2-step procedure. Holmberg et al., *Bioconjugate Chem.*, 4: 570–73 (1993). This simple method involves allylation of the dextran's hydroxyl groups, followed by a free-radical type addition of borocaptate. This method has been found to incorporate 100–125 boron cages, or 1200–1500 boron atoms, per dextran chain. The product obtained by this method is water soluble. According to Holmberg et al., supra, 70% of the hydroxyls were allylated and a 50% efficiency in the boronation of allyl dextran resulted in the conjugate having boron content of 150 $\mu$g boron/mg and a sulfur content of 1.5–4%. This corresponds to 100–120 boron cages, or 1200–1500 boron atoms, per dextran chain.

In particular, dextran (2 g, 70 kD) was allylated in aqueous solution with 29 mmol of allyl bromide in the presence of 12.5 mmol of sodium hydroxide for 2 h at 60° C. After this time the reaction mixture was acidified, repeatedly precipitated from acetone, washed several times with ethanol and finally dialyzed. The intermediate product was then made basic with 40 mmol of sodium hydroxide and reacted with 2.8 g of 6-bromohexanoic acid at 70–80° C. for 5 h. The solution was cooled, acidified and purified by dialysis.

The doubly derivatized dextran is boronated by reaction of dextran allyl groups with sodium borocaptate ('BSH' or $Na_2B_{12}H_{11}SH$; di-sodium undecahydro-mercapto-closo-dodecacarborate; Boron Biologicals, Raleigh, N.C.). Briefly, allyl dextran (20 mg) was reacted with 30 mg of sodium borocaptate and 20 mg of ammonium persulfate in 2 mL of water for 3 h at 50° C. The intermediate product is purified by PD-10 column chromatography and by repeated dialysis against water.

Boron content of the sulfhydrylborane-dextran conjugate is determined using ICP-atomic emission spectroscopy, as well as from sulfur content. Sulfur analysis indicated the presence of 124.3 boron cages while microanalysis for boron content gives a figure of 137 boron cages (1644 boron atoms) per mole of dextran. Boron determinations of non-biological samples can be carried out by commercial outlets (Galbraith Laboratories).

The carboxylic acid derivatized boronated dextran-70 (12.5 mg) was treated with 1-ethyl-3-(3-dimethylamino-propyl) carbodiimide (12.5 mg) and a fifty-fold excess of ethylene diamine at pH 5.3 for 4 h at room temperature. Excess reactants were removed from the polymeric intermediate by repeated filtration through a Centricon-30 membrane and the purified intermediate was buffer-exchanged into 0.1 M phosphate buffer at pH 7.7. This material was reacted with a fifteen-fold molar excess of sulfosuccinimido biotin for one hour and finally purified using a Centricon-30 membrane. HABA assay indicated that the biotinylated-boronated-dextran-70 contained approximately two biotin moieties per polymeric unit.

While 70 KD molecular weight dextran is used in this example, in vivo pharmacokinetics of the boronated dextran may make the use of either higher or lower molecular weight dextran preferable.

2. Carboxyalkylation of sulfhydrylborane-dextran conjugate:

To react with an amine-containing biotin analog, the dextran conjugate is first derivatized with 6-bromohexanoic acid to introduce the necessary carboxylic acid groups. Carboxyalkylation and the allylation reaction described above are both chemically the same type of alkylation reaction. These two reactions can be combined in one operation by first reacting dextran, under basic conditions, with allyl bromide, and then reacting with bromohexanoic acid. A similar tandem operation has been described for the conjugation of mitomycin with an antibody using dextran as intermediate carrier. Noguchi et al., *Bioconj. Chem.*, 3: 132–37 (1992). The order of alkylation is designed to limit the level of carboxylic acid groups introduced so as to achieve a biotin-dextran ratio of about one in the next step. The extent of carboxyalkylation is determined by titration with sodium methoxide. Any slight reduction in the number of boron atoms introduced as a result of this "double derivatization" should not be too worrisome due to the large number of boron atoms loadable by this method, and due to the 4-fold amplification of boron localization per mole of the SAv-IgG conjugate localized at tumor sites.

3. Biotinylation of sulfhydrylborane-dextran (Scheme 1):

A preferred embodiment of the present invention uses a specially designed amine-containing biotin analog (compound 7 of Scheme 1). This compound has a spacer arm between the biotin moiety and the amine terminus, and has a N-methyl substitution at the biotin peptide bond. Alternatively, a biotinidase-resistant biotin analog comprising a biotin peptide-bonded to an unnatural D-amino acid, and further terminating in an amino group for conjugation to carboxyl-substituted dextran borocaptate, may be used. These characteristics of the specific biotin-peptide bond prevent or minimize recognition by serum biotinidases, and the compounds are therefore more stable. Evangelatos et al., *Analyt. Biochem.*, 196: 385–89 (1991).

The amine-containing biotinylation agent is condensed with carboxyalkylated sullhydrylborane-dextran using water soluble carbodiimide ('EDC') and N-hydroxy sulfosuccinimide at a pH of about 6 at room temperature. The structure of the requisite final product is shown as compound 4 in Scheme 1.

The extent of amide formation may be controlled by varying the molar excess of amine used. Noguchi et al., supra. Such manipulation can be used to control the amount of biotin introduced, with the goal of introducing an average of about 1 biotin moiety per dextran chain. Final molar substitution ratios are derived from determinations of biotin-dextan and boron-dextran ratios, and from binding to known concentrations of streptavidin.

II. METHODS FOR TARGETING BORON ATOMS TO TUMOR CELLS

Methods using an anti-CEA x anti-carborane bispecific antibody:

The following example illustrates a three-step pretargeting method using a bispecific antibody and a clearing agent before the boron compound is administered. The three steps are as follows:

Step 1: A bispecific monoclonal antibody comprising an anti-CEA determinant and an anti-carborane determinant is administered to a cancer patient, and allowed to localize at tumor sites.

Step 2: The circulating conjugate is cleared using a galactosylated anti-idiotypic monoclonal antibody specific for the anti-CEA determinant of the bispecific antibody described above.

Step 3: A carborane-dextran-boron polymer comprising from about 1200 to about 1500 boron atoms is administered, and localizes at the tumor sites due to the affinity between the carborane and the anti-carborane determinant of the bispecific monoclonal antibody localized at the tumor site in step 1.

Once the boron has localized at the tumor site, it is irradiated in accordance with conventional BNCT methods.

Another three-step pre-targeting method using a bispecific antibody and a clearing agent after the boron compound is administered is as follows:

Step 1: A bispecific monoclonal antibody comprising an anti-CEA determinant and an anti-carborane determinant is administered to a cancer patient, and allowed to localize at tumor sites.

Step 2: A carborane-dextran-boron polymer comprising from about 1200 to about 1500 boron atoms is administered, and localizes at the tumor sites due to the affinity between the carborane and the anti-carborane determinant of the bispecific monoclonal antibody localized at the tumor site in step 1.

Step 3: Circulating carborane-dextran-boron polymer is cleared using a monoclonal antibody specific for the same hapten of the boron compound that is bound by the anti-carborane determinant of the bispecific monoclonal antibody used in Step 1.

Once non-localized boron has been cleared, localized boron is irradiated in accordance with conventional BNCT methods.

Methods using an anti-CEA x anti-biotin bispecific antibody:

The following example illustrates a three-step pre-targeting method using a bispecific antibody and a clearing agent before the boron compound is administered. The three steps are as follows:

Step 1: A bispecific monoclonal antibody comprising an anti-CEA determinant and an anti-biotin determinant is administered to a cancer patient, and allowed to localize at tumor sites.

Step 2: The circulating conjugate is cleared using a galactosylated anti-idiotypic monoclonal antibody specific for the anti-CEA determinant of the bispecific antibody described above.

Step 3: A biotin-dextran-boron compound comprising from about 1200 to about 1500 boron atoms is administered, and localizes at the tumor sites due to the affinity between the biotin and the anti-biotin determinant of the bispecific monoclonal antibody localized at the tumor site in step 1.

Once the boron has localized at the tumor site, it is irradiated in accordance with conventional BNCT methods.

A three-step pre-targeting method using a bispecific antibody and a clearing agent after the boron compound is administered is as follows:

Step 1: A bispecific monoclonal antibody comprising an anti-CEA determinant and an anti-biotin determinant is administered to a cancer patient, and allowed to localize at tumor sites.

Step 2: A biotin-dextran-boron compound comprising from about 1200 to about 1500 boron atoms is administered, and localizes at the tumor sites due to the affinity between the biotin and the anti-biotin determinant of the bispecific monoclonal antibody localized at the tumor site in step 1.

Step 3: Circulating biotin-dextran-boron polymer is cleared using a monoclonal antibody specific for the same hapten of the boron compound that is bound by the anti-biotin determinant of the bispecific monoclonal antibody used in Step 1.

Once non-localized boron has been cleared, localized boron is irradiated in accordance with conventional BNCT methods.

Methods using a multivalent, multispecific targeting composition:

The following example illustrates a three-step pre-targeting method using a multivalent, multispecific targeting composition and a clearing agent before the boron compound is administered. The three steps are as follows:

Step 1: A multivalent, multispecific targeting composition, comprising a F(ab')$_2$ fragment comprising anti-CEA determinants and a Fab fragment comprising an anti-carborane determinant, is administered to a cancer patient, and allowed to localize at tumor sites.

Step 2: The circulating conjugate is cleared using an anti-idiotypic monoclonal antibody specific for the anti-CEA determinants of the multivalent, multispecific targeting composition described above. The clearing antibody may be galactosylated to achieve rapid clearance as described above.

Step 3: A carborane-dextran-boron polymer comprising about 1200 to about 1500 boron atoms is administered, and localizes at the tumor sites due to the affinity between the carborane and its determinant on the multivalent, multispecific targeting composition localized at the tumor site in step 1.

Once the boron has localized at the tumor site, it is irradiated in accordance with conventional BNCT methods.

Another three-step pre-targeting method using a multivalent, multispecific targeting composition and a clearing agent after the boron compound is administered is as follows:

Step 1: A multivalent, multispecific targeting composition, comprising a F(ab')$_2$ fragment comprising anti-CEA determinants and a Fab fragment comprising an anti-carborane determinant, is administered to a cancer patient, and allowed to localize at tumor sites.

Step 2: A boron compound comprising a particular antigen which is the hapten of the antibody described above and from about 1200 to about 1500 boron atoms is administered, and localizes at the tumor sites due to the affinity between the carborane and its determinant on the multivalent, multispecific targeting composition localized at the tumor site in step 1.

Step 3: Circulating carborane-dextran-boron polymer is cleared using a monoclonal antibody specific for the same hapten of the boron compound that is bound by the anti-carborane determinant of the multivalent, multispecific targeting composition used in Step 1.

Once non-localized boron has been cleared, localized boron is irradiated in accordance with conventional BNCT methods.

It will be apparent to those skilled in the art that various modifications and variations can be made to the processes and compositions of this invention. Thus, it is intended that the present invention cover the modifications and variations of this invention provided they come within the scope of the appended claims and their equivalents.

SCHEME-1

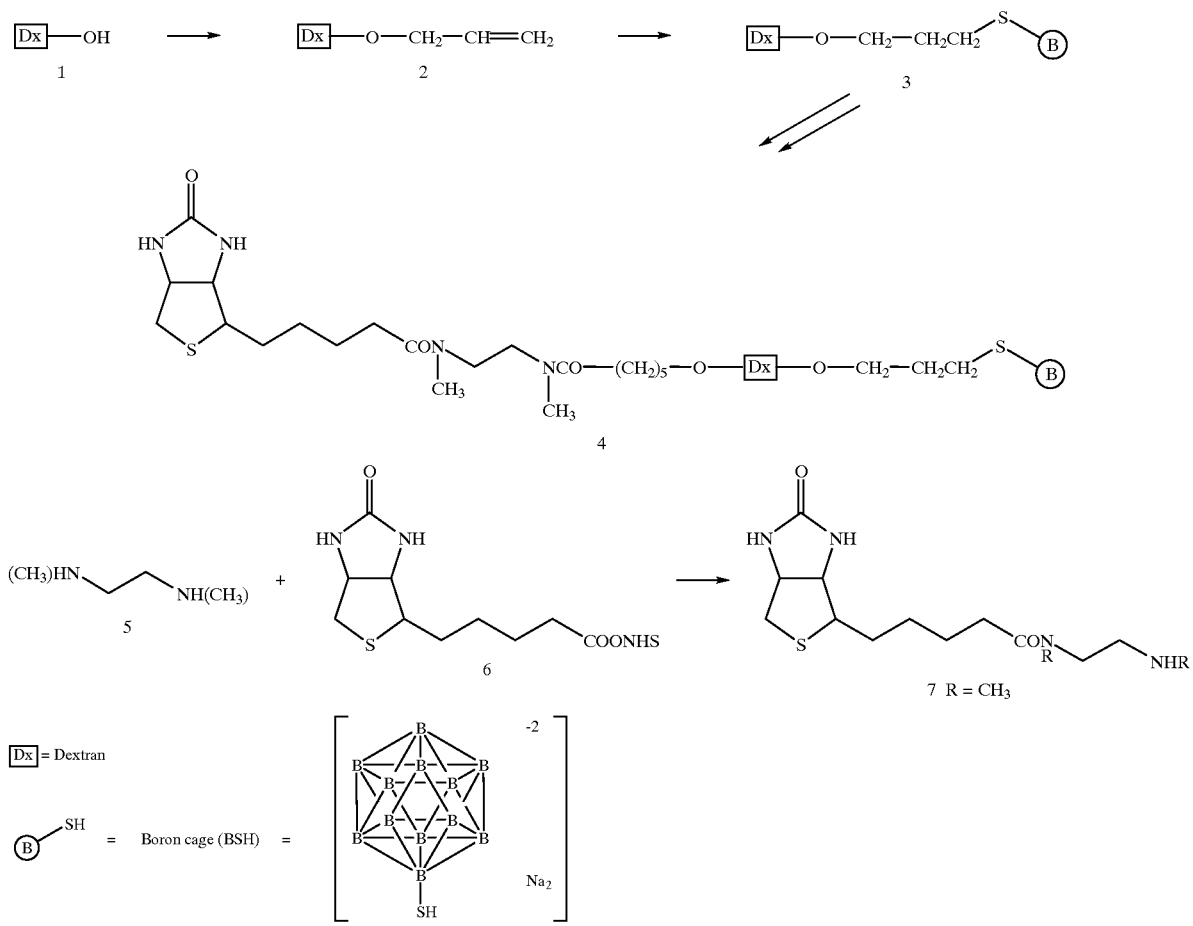

What is claimed is:

1. A method for targeting boron atoms to tumor cells in a patient, comprising the steps of:
   (A) administering to said patient a targeting composition comprising a conjugate of
      (i) at least one first antibody or antigen-binding antibody fragment which selectively binds to an antigen produced by or associated with the tumor cells and present at the tumor cells, and
      (ii) at least one second antibody or antibody fragment which specifically binds to a non-boron containing hapten on the carrier portion of a boron-carrier compound and allowing said conjugate to localize at said tumor cells;
   (B) optionally, administering to said patient a first clearing composition, and allowing said clearing composition to clear non-localized conjugate from circulation;
   (C) administering to said patient said boron-carrier compound and allowing said boron-carrier compound to localize at said tumor cells;
   (D) optionally, administering to said patient a second clearing composition, and allowing said clearing composition to clear non-localized boron-carrier compound from circulation.

2. The method of claim 1, wherein said conjugate comprises a bi-specific antibody.

3. The method of claim 1, wherein said conjugate comprises a polyspecific antibody.

4. The method of claim 3, wherein said polyspecific antibody comprises a plurality of determinants that specifically bind to the same or different epitopes of an antigen produced by or associated with the tumor cells, or that bind to different antigens produced by or associated with the tumor cells.

5. The method of claim 3, wherein said polyspecific antibody comprises a plurality of determinants that specifically bind to the same or different epitopes of said boron-carrier compound.

6. The method of claim 1, wherein said first antibody or antibody fragment is a monoclonal antibody or a fragment of a monoclonal antibody.

7. The method of claim 1, wherein said second antibody or antibody fragment is a monoclonal antibody or a fragment of a monoclonal antibody.

8. The method of claim 1, wherein said first antibody or antibody fragment is a humanized antibody or a fragment of a humanized antibody.

9. The method of claim 1, wherein said second antibody or antibody fragment is a humanized antibody or a fragment of a humanized antibody.

10. The method of claim 1, wherein said first antibody or antibody fragment is an anti-CEA antibody or a CEA-binding fragment of an anti-CEA antibody.

11. The method of claim 1, wherein said boron-carrier compound comprises a moiety selected from the group consisting of biotin, DTPA, histamine-succinate, fluorescein, rhodamine, dinitrophenyl (DNP), dextran and polyhistidine, and said second antibody or antibody fragment comprises an antibody or antibody fragment that specifically binds to a non-boron containing hapten on said moiety.

12. The method of claim 1, wherein at least one of said optional first and second clearing agents is an antibody.

13. The method of claim 12, wherein said antibody is galactosylated.

14. The method of claim 1, wherein said optional first clearing composition of step (B) is administered.

15. The method of claim 14, wherein said boron-carrier compound of step (C) is administered within about 2 to about 24 hours after said clearing composition of step (B) is administered.

16. The method of claim 14, wherein said first clearing composition of step (B) comprises an antibody that is anti-idiotypic to said first antibody or antibody fragment.

17. The method of claim 1, wherein said optional second clearing composition of step (D) is administered.

18. The method of claim 17, wherein said second clearing composition of step (D) comprises an antibody specific for the non-boron containing hapten on said boron-carrier compound that is bound by said second antibody or antibody fragment.

19. The method of claim 2, wherein said boron-carrier compound comprises dextran derivatized with from about 1200 to about 1500 boron atoms.

20. The method of claim 1, wherein said boron-carrier compound is radiolabeled with a detectable label.

21. The method of claim 20, further comprising the step of detecting said detectable label of said boron-carrier compound, thereby determining the location of said compound.

22. The method of claim 21, further comprising the step of irradiating the boron atoms of said boron-carrier compound localized at said tumor cells, after said detectable label is detected.

23. The method of claim 1, wherein said boron-carrier compound is administered within about 48 to about 240 hours after said targeting composition of step (A) is administered.

24. The method of claim 1, wherein said clearing composition of step (B) is not administered, and wherein said boron-carrier compound of step (C) is administered within about 5 to about 20 days after said targeting composition of step (A) is administered.

25. The method of claim 1, wherein up to about 6000 boron atoms per molecule of antibody administered are localized at said tumor cells.

26. The method of claim 1, further comprising the step of irradiating the boron atoms of said boron-carrier compound localized at said tumor cells, thereby effecting BNCT of said tumor cells.

27. A sterile, injectable composition for human use comprising a composition for use in targeting boron atoms to tumor cells, comprising a conjugate of
  (i) at least one first antibody or antigen-binding antibody fragment which selectively binds to an antigen produced by or associated with the tumor cells and present at the tumor cells, and
  (ii) at least one second antibody or antibody fragment which specifically binds to a non-boron containing hapten on the carrier portion of a boron-carrier compound.

28. The composition of claim 27, wherein said first antibody or antibody fragment is an anti-CEA antibody or a CEA-binding fragment of an anti-CEA antibody.

29. The composition of claim 28, wherein said boron-carrier compound comprises a moiety selected from the group consisting of biotin, DTPA, histamine-succinate, fluorescein, rhodamine, dinitrophenyl (DNP), dextran and polyhistidine, and said second antibody or antibody fragment comprises an antibody or antibody fragment that specifically binds to a non-boron containing hapten on said moiety.

30. A kit suitable for use in a method for targeting boron atoms to tumor cells in a patient, the kit comprising:
  (A) a sterile, injectable preparation of a targeting composition comprising a conjugate of
    (i) at least one first antibody or antigen-binding antibody fragment which selectively binds to an antigen produced by or associated with the tumor cells and present at the tumor cells, and
    (ii) at least one second antibody or antibody fragment which specifically binds to a non-boron containing hapten on the carrier portion of a boron-carrier compound;
  (B) optionally, a first clearing composition;
  (C) said boron-carrier compound; and
  (D) optionally, a second clearing composition.

31. The kit of claim 30, wherein said first antibody or antibody fragment is an anti-CEA antibody or a CEA-binding fragment of an anti-CEA antibody.

32. The kit of claim 30, wherein said boron-carrier compound comprises a moiety selected from the group consisting of biotin, DTPA, histamine-succinate, fluorescein, rhodamine, dinitrophenyl (DNP), dextran and polyhistidine, and said second antibody or antibody fragment comprises an antibody or antibody fragment that specifically binds to a non-boron containing hapten on said moiety.

33. The kit of claim 30, wherein said boron-carrier compound comprises dextran derivatized with from about 1200 to about 1500 boron atoms.

* * * * *